US006598307B2

(12) United States Patent
Love et al.

(10) Patent No.: US 6,598,307 B2
(45) Date of Patent: Jul. 29, 2003

(54) DEVICE AND METHOD FOR ASSESSING THE GEOMETRY OF A HEART VALVE

(76) Inventors: Jack W. Love, 785 Carosam Rd., Santa Barbara, CA (US) 93110; James G. Hanlon, 1642 E. Regent St., Camarillo, CA (US) 93010

( * ) Notice: Subject to any disclaimer, the term of this patent is extended or adjusted under 35 U.S.C. 154(b) by 0 days.

(21) Appl. No.: 09/928,740

(22) Filed: Aug. 13, 2001

(65) Prior Publication Data

US 2002/0020074 A1 Feb. 21, 2002

Related U.S. Application Data

(63) Continuation-in-part of application No. 09/716,140, filed on Nov. 17, 2000.
(60) Provisional application No. 60/165,977, filed on Nov. 17, 1999.

(51) Int. Cl.⁷ ................................................ A61B 5/103
(52) U.S. Cl. ........................ 33/512; 33/555.1; 33/542; 600/587; 623/2; 623/2.11
(58) Field of Search ........................ 33/511, 512, 555.1, 33/501.45, 542, 543; 600/587, 29, 30, 31, 32, 593, 591; 623/2, 2.11

(56) References Cited

U.S. PATENT DOCUMENTS

| | | |
|---|---|---|
| 3,320,972 A | 5/1967 | High et al. |
| 3,655,306 A | 4/1972 | Ross et al. |
| 4,211,241 A * | 7/1980 | Kaster et al. .................. 33/512 |
| 4,470,157 A | 9/1984 | Love |
| 4,731,075 A | 3/1988 | Gallo Mezo et al. |
| 4,960,424 A | 10/1990 | Grooters |
| 5,147,391 A | 9/1992 | Lane |
| 5,156,621 A | 10/1992 | Navia et al. |
| 5,163,955 A | 11/1992 | Love et al. |
| 5,197,979 A | 3/1993 | Quintero et al. |
| 5,258,021 A | 11/1993 | Duran |
| 5,297,564 A | 3/1994 | Love |

(List continued on next page.)

FOREIGN PATENT DOCUMENTS

| | | |
|---|---|---|
| EP | 0 581 233 | 2/1994 |
| FR | 2399 832 | 9/1979 |
| WO | WO 92/03990 | 3/1992 |
| WO | WO 92/12690 | 8/1992 |
| WO | WO 92/13502 | 8/1992 |
| WO | WO 93/18721 | 9/1993 |
| WO | WO 95/16411 | 6/1995 |

OTHER PUBLICATIONS

1998 Jack W. Love Autologous pericardial reconstruction of semilunar valves, The Journal of Heart Valve Disease 1998; 7:40–47.

(List continued on next page.)

*Primary Examiner*—Diego Gutierrez
*Assistant Examiner*—Yaritza Guadalupe
(74) *Attorney, Agent, or Firm*—Bryan Cave LLP

(57) ABSTRACT

A sizer for assessing the geometry of a heart valve annulus including a handle portion for holding the sizer and a sizing portion. The sizing portion is preferably in the shape of an arch having an apex and two legs, each of which has a base adjoining the handle portion. The legs of the arched sizing portion are separated from each other by a predetermined distance that corresponds to the expected separation of commissures of a normal heart valve annulus. The height of the arch (measured from the base of each leg to the apex) corresponds to a predetermined leaflet height that approximates the expected height of a leaflet of a normal heart valve. For aortic valve reconstruction, the instrument is inserted into the opened aortic root following removal of the native valve tissue and is used to assess the distance between the commissures, the leaflet height, and the symmetry of the commissures of the exposed valve annulus.

24 Claims, 5 Drawing Sheets

U.S. PATENT DOCUMENTS

| | | |
|---|---|---|
| 5,326,370 A | 7/1994 | Love et al. |
| 5,326,371 A | 7/1994 | Love et al. |
| 5,336,258 A | 8/1994 | Quintero et al. |
| 5,344,442 A | 9/1994 | Deac |
| 5,352,240 A | 10/1994 | Ross |
| 5,370,685 A | 12/1994 | Stevens |
| 5,376,112 A | 12/1994 | Duran |
| 5,411,552 A | 5/1995 | Andersen et al. |
| 5,423,887 A | 6/1995 | Love et al. |
| 5,425,741 A | 6/1995 | Lemp et al. |
| 5,449,384 A | 9/1995 | Johnson |
| 5,480,424 A | 1/1996 | Cox |
| 5,489,296 A | 2/1996 | Love et al. |
| 5,489,298 A | 2/1996 | Love et al. |
| 5,503,638 A | 4/1996 | Cooper et al. |
| 5,509,930 A | 4/1996 | Love |
| 5,531,784 A | 7/1996 | Love et al. |
| 5,531,785 A | 7/1996 | Love et al. |
| 5,571,174 A | 11/1996 | Love et al. |
| 5,584,878 A | 12/1996 | Love et al. |
| 5,662,705 A | 9/1997 | Love et al. |
| 5,716,399 A | 2/1998 | Love |
| 5,755,782 A | 5/1998 | Love et al. |
| 5,814,096 A * | 9/1998 | Lam et al. .................... 600/36 |
| 6,019,739 A * | 2/2000 | Rhee et al. .................... 33/512 |
| 6,042,554 A * | 3/2000 | Rosenman et al. ........ 623/2.11 |
| 6,129,758 A | 10/2000 | Love |
| 6,193,758 B1 * | 2/2001 | Huebner .................... 606/102 |
| 6,231,601 B1 * | 5/2001 | Myers et al. .............. 623/2.11 |
| 6,322,526 B1 * | 11/2001 | Rosenman et al. ......... 600/587 |
| 6,350,281 B1 * | 2/2002 | Rhee ........................... 33/512 |
| 6,383,147 B1 * | 5/2002 | Stobie ........................ 623/2.1 |

OTHER PUBLICATIONS

Aug. 20, 1993 P. Zioupos and J.C. Barbenel Mechanics of native bovine pericardium. I. The multiangular behavior of strength and stiffness of the tissue. Biomaterials 1994, vol. 15, pp. 366–373.

1994 P. Zioupous, J.C. Barbenel, J. Fisher Anisotropic elasticity and strength of glutaraldehyde fixed bovine pericardium for use in pericardial bioprosthetic valves, Journal of Biomedical Materials Research, vol. 28, 49–57 (1994).

1993 P. Zioupos, J.C. Barbenel, J. Fisher, D.C. Wheatley Changes in mechanical properties of bioprosthetic valve leaflets made of bovine pericardium, as a result of long–term mechanical conditioning in vitro and implantation in vivo, Journal of Materials Science: Materials in Medicine, 531–537, 1993.

1974 W. Milton Swanson, Richard E. Clark Dimensions and Geometric Relationships of the Human Aortic Valve as a Function of Pressure, Circulation Research, vol. 35 (1974).

1999 Steven Kahn Cedars–Sinai Medical Center Prosthetic Valve Information Page, Steven Kahn, M.D., Division of Cardiothoracic Surgery, Cedars–Sinai Medical Center.

Aug. 13, 2000 James G. Hanlon, Robert W. Suggitt, Jack W. Love Advances in Seminular Heart Valve Reconstruction, World Congress of International Society of Cardio–Thoracic Surgeons, Aug. 13–16, 2000.

* cited by examiner

DEVICE AND METHOD FOR ASSESSING THE GEOMETRY OF A HEART VALVE

CROSS REFERENCE TO RELATED APPLICATION

This application is a continuation-in-part of U.S. application Ser. No. 09/716,140, filed Nov. 17, 2000, which claims the benefit of U.S. Provisional Application No. 60/165,977, filed Nov. 17, 1999.

FIELD OF THE INVENTION

This invention relates to measuring instruments and methods and is particularly directed to instruments and methods used to measure the size and dimensions of heart valves in the surgical operating room at the time of heart valve reconstruction or replacement.

BACKGROUND OF THE INVENTION

When a surgeon must replace one or more of a patient's heart valves because of disease or defect of the native valve(s), the surgeon must identify the diameter of the patient's aorta in order to select the correct size replacement heart valve. The measurement of heart valve diameter in the operating room is typically done with some type of plug gauge. Gradated sizes of plug gauges, typically in 2 millimeter increments are used to find the best fit for any given valve annulus. The advent of homograft valves and, more recently, methods for reconstructing heart valves, makes it desirable to determine more than simply the best fit diameter. For operations involving the use of homograft valves, stentless heterograft valves, and any one of several methods of aortic or pulmonic heart valve reconstruction being used, it is also desirable to assess the height of the leaflets, the distance between the commissures and the symmetry, or lack thereof, of the spacing of the valve commissures. Such methods of valve reconstruction are described, for example, in Love U.S. Pat. No. 5,716,399, Love U.S. Pat. No. 6,129,758, and copending U.S. application Ser. No. 09/330,689 of Love, et al. (each of which is incorporated herein by reference in its entirety). To facilitate such methods of valve reconstruction, there is a strong need for instruments and methods that can be used in the operating room to quickly and effectively assess valve annulus geometry more completely than has been possible in the past. The instruments and methods of the present invention satisfy these needs and provide other advantageous results.

SUMMARY OF THE INVENTION

The present invention is comprised of methods and instruments that can be used to measure the diameter of the valve annulus at the commissural level, the sino-tubular diameter, to compare the height and lines of attachment of the individual leaflets with reference to a normalized geometry, and to determine the symmetry of the valve commissures.

One preferred embodiment of the present invention comprises a circular piece with three equally spaced radial spokes that converge in the center to a socket to which a handle can be attached. Curved legs that correspond to the geometry of the normal native valve leaflet anatomy, as described in published medical articles, are attached to the circular piece.

In a typical operation to replace or to reconstruct an aortic or pulmonic valve, the diseased native valve is removed down to the annulus of the valve. After this has been done, the valve is sized. With the present invention, sizers of graded dimensions are used until the best-fit diameter at the commissural level is determined. With that sizer inserted in the aortic or pulmonic root, the height of each leaflet from its base to the apex of its commissures can be compared with the expected dimensions for that valve, based on published dimensions. The symmetry of the valve can be judged by aligning any given radial spokes of the circular piece with one commissure, and then noting the spacing of the remaining two commissures. The radial spokes each have a width that corresponds to an arc of the circle that encompasses the normal expected variation from perfect symmetry. Deviations from expected normal leaflet height or symmetry can be readily appreciated and used to increase the precision of the planned surgical procedure.

Another version of the present invention includes a handle portion for holding the sizer and a sizing portion adjoining the handle portion. In one embodiment, the sizing portion has a predetermined distance indicator for assessing the distance between the commissures of the annulus. The sizing portion is placed adjacent to two of the commissures and the predetermined distance on the sizing portion is compared to the distance between the two commissures. In another embodiment, the sizing portion has a predetermined height indicator for assessing the leaflet height of the annulus. The sizing portion is placed along the contoured line of valve leaflet attachment of the annulus so that the predetermined height on the sizing portion can be compared to the leaflet height of the annulus.

A presently preferred embodiment includes an arch-shaped sizing portion substantially conforming to the shape of the contoured line of valve leaflet attachment of the annulus. The sizing portion is in the shape of an arch having an apex and two legs, each of which has a base adjoining the handle portion. The base of each leg is preferably bent such that the sizing portion is angled to conform to the conical shape of the valve annulus. The legs of the arched sizing portion are separated from each other by a predetermined distance. The predetermined distance separating the legs corresponds to the expected separation of commissures of a normal heart valve annulus having approximately the same diameter as the valve annulus being assessed. The height of the arch (measured from the base of each leg to the apex) preferably corresponds to a predetermined leaflet height. This predetermined height preferably approximates the expected height of a leaflet of a normal heart valve having approximately the same diameter as the valve annulus being assessed.

The distance between the commissures is assessed by inserting the sizing portion is into the heart valve annulus and placing the two legs of the arch adjacent to two of commissures of the valve annulus. The distance between the two commissures is compared to the predetermined distance between the two legs. For a tri-leaflet valve, symmetry can be assessed by comparing the three intercommissural distances; in a symmetric root these distances should be in close agreement. Leaflet height is assessed by placing the sizing portion of the device along the contour of the line of valve leaflet attachment and comparing the leaflet height of the heart valve annulus to the height of the arch.

The present invention further encompasses an instrument and method for marking a contoured line of valve leaflet attachment of a heart valve annulus. The instrument includes a handle portion and a marking portion. The marking portion conforms in shape to the contoured line of valve leaflet attachment and preferably includes a wettable textured region for retaining a marking material such as a dye. A marking material is applied to the marking portion. The marking portion is then inserted into the annulus and placed along the contoured line of valve leaflet attachment to mark the line of leaflet attachment.

The drawings are provided for illustrative purposes only and may not be used to unduly limit the scope of the invention.

DETAILED DESCRIPTION OF THE INVENTION

Figure 1:
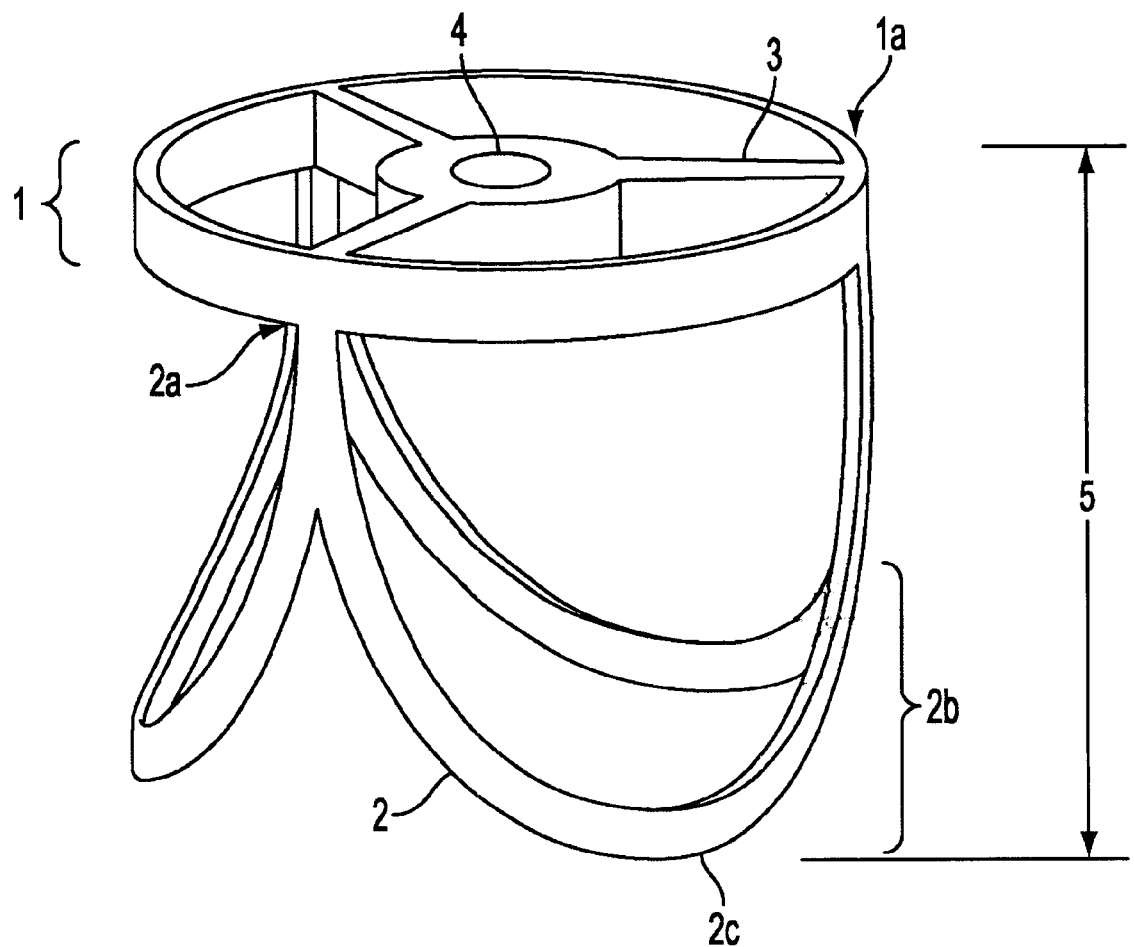
FIG. 1 is an oblique view from the side of a sizer of one embodiment of the present invention.
Figure 2:
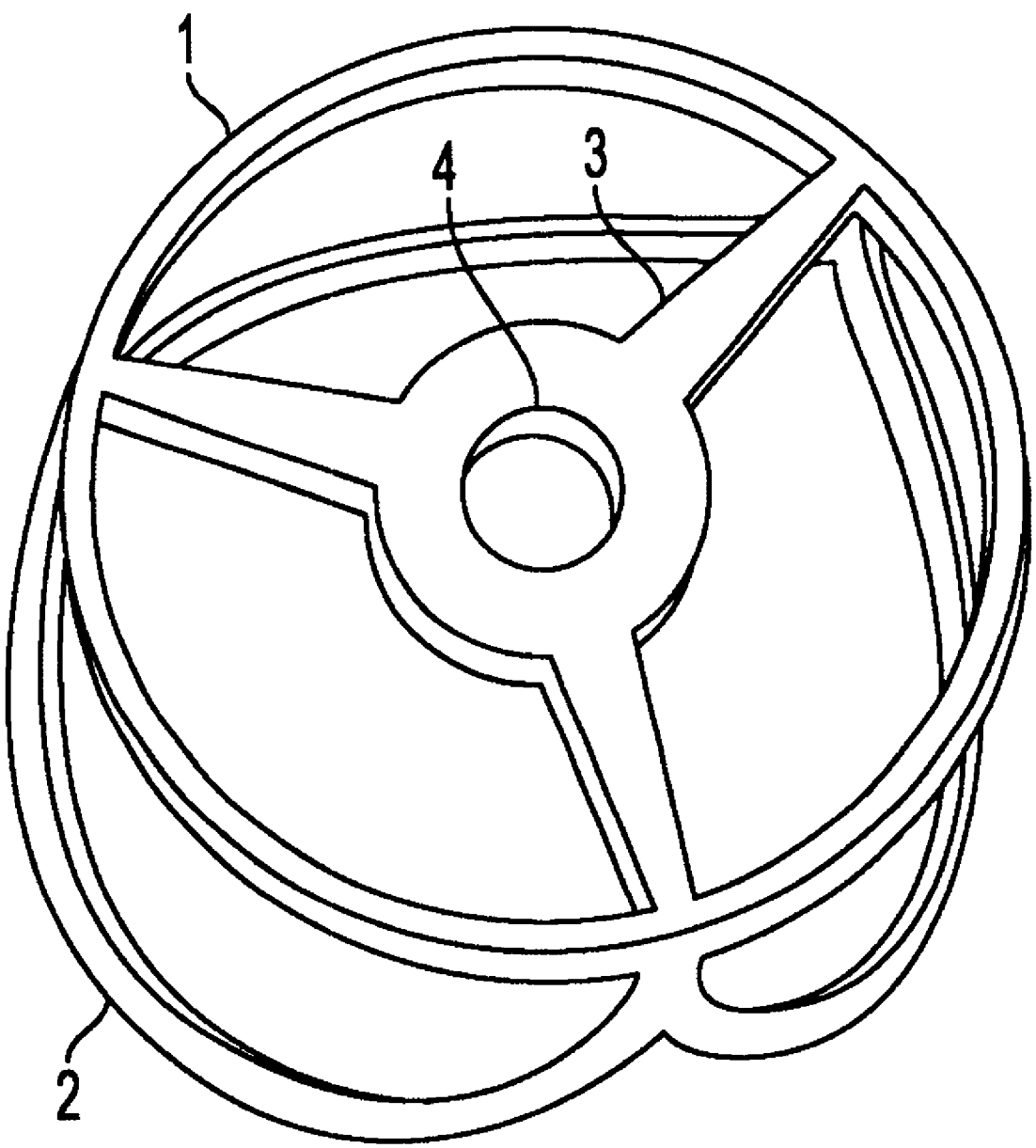
FIG. 2 is an oblique view from the top of the sizer of FIG. 1.

FIG. 1 and FIG. 2 represent two views of a sizer for assessing the geometry of a heart valve annulus by measuring annulus size, leaflet height, and leaflet symmetry of semilunar heart valves and is one preferred embodiment of the present invention. The instrument is preferably molded, cast or machined as a single unit, preferably from stainless steel or a biocompatible thermoplastic material that can be readily sterilized and discarded after single use. The material preferably has sufficient rigidity to maintain its shape during the sizing procedure, but also a degree of malleability to make it easy to insert into, apply marking dye, and withdraw from the valve root without damaging the tissue. All edges that contact tissue are round and smooth to avoid damage to the tissue.

In FIG. 1, the sizing portion 1 is used to measure the diameter of the valve orifice at the commissural level. The sizing portion 1 is preferably circular. One or more legs 2 define the contoured line of attachment of a normal leaflet. Each leg preferably has an arched shape substantially conforming to the expected contour of a normal heart valve having a diameter substantially equivalent to the diameter of the sizing portion. As used herein the term "normal heart valve" generally refers to a heart valve having standard geometry and dimensions. However, the term "normal heart valve" is intended to broadly encompass any heart valve dimensions used as a standard of comparison. As used herein the term "diameter substantially equivalent to the measured diameter" is used broadly to refer to a diameter that is the same as, corresponding to, within a range of, or at a set variance from the measured diameter. Each leg has a proximal end 2a attached to the sizing portion 1 and a distal end 2b. The distal end 2b preferably has an arced shape with an apex 2c. Leaflet height is the dimension 5 which represents the distance from the top of the circular sizing portion 1 to the apex 2c of leg 2. This is a distance that is a ratio of the diameter of the circular sizing portion 1.

Symmetry is assessed by aligning one of a plurality of radial spokes 3 of the sizing portion with a commissure of the native valve, and then comparing the alignment of the remaining two commissures with the other two radial spokes of the circular piece. Each spoke 3 is preferably connected to the perimeter 1a of the circular sizing portion 1 such that the width of each spoke at the perimeter 1a corresponds to an arc width on the perimeter 1a that corresponds to an acceptable small normal variation from perfect symmetry. The three spokes 3 are united in the center of the circular sizing portion 1 by a socket 4 to which a handle can be removeably attached, either by a threaded connection or by some other quick connect-disconnect device.

In FIG. 2, some of these same components are identified. The circular sizing portion 1 has the curved legs 2 to mark the leaflet line of attachment to the annulus. The radial spokes 3 are joined to the central socket 4.

The sizer with handle attached is placed in the aortic or pulmonic root so that the circular sizing portion is at the level of the commissures. Individual leaflet height and the line of leaflet attachment to the annulus are determined by comparing the curved legs 2 with the native valve geometry. Commissural symmetry is assessed by aligning one spoke with any one commissure and then noting the relationship of the other spokes with the other commissures. If all three commissures align within the width of the spokes where they intersect with the perimeter 1a of the circular portion 1, the native valve is symmetrical within normal the normal range of variation.

Figure 3:
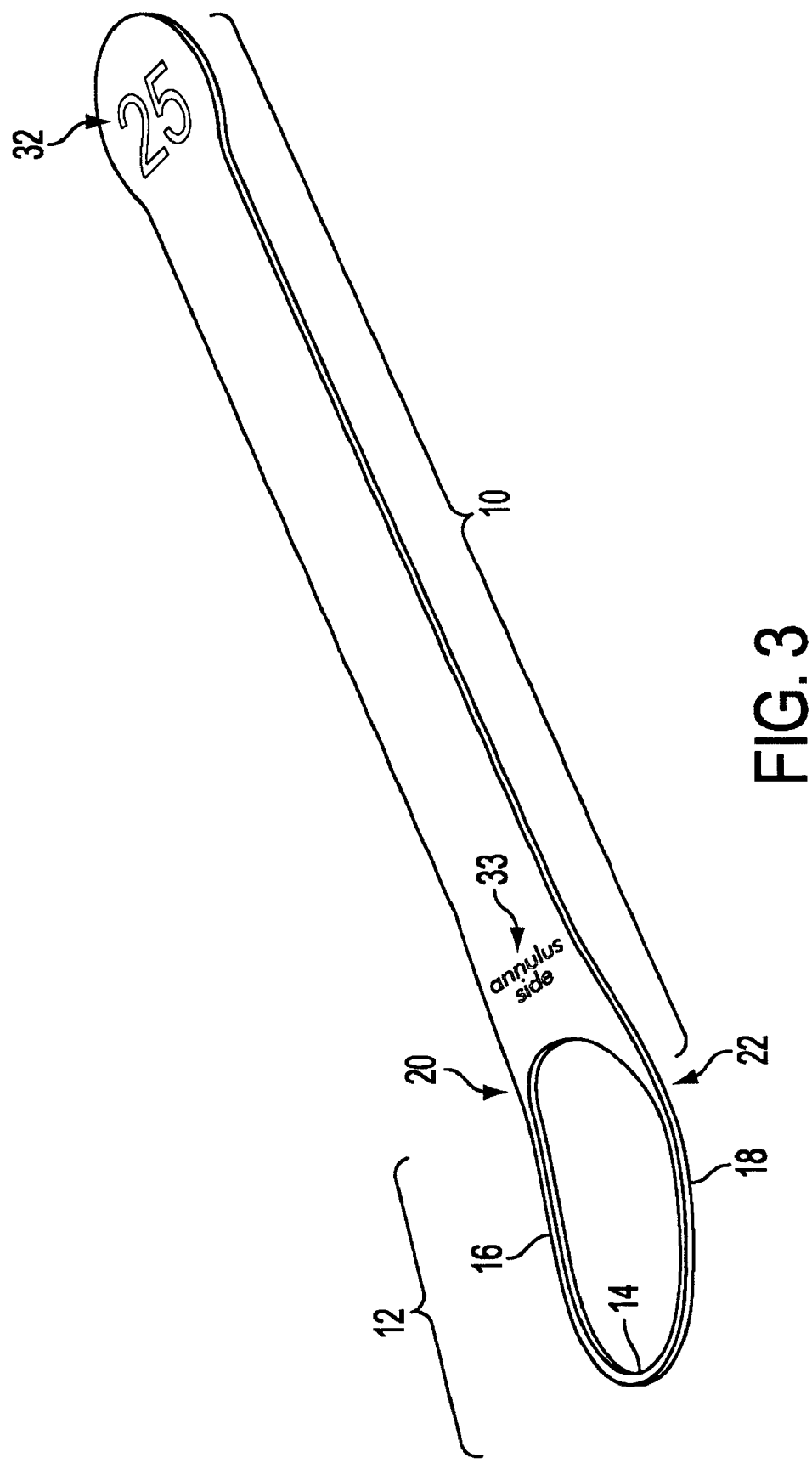
FIG. 3 is a top perspective view of an embodiment of the instrument of the present invention have an arch-shaped sizing portion.
Figure 4:
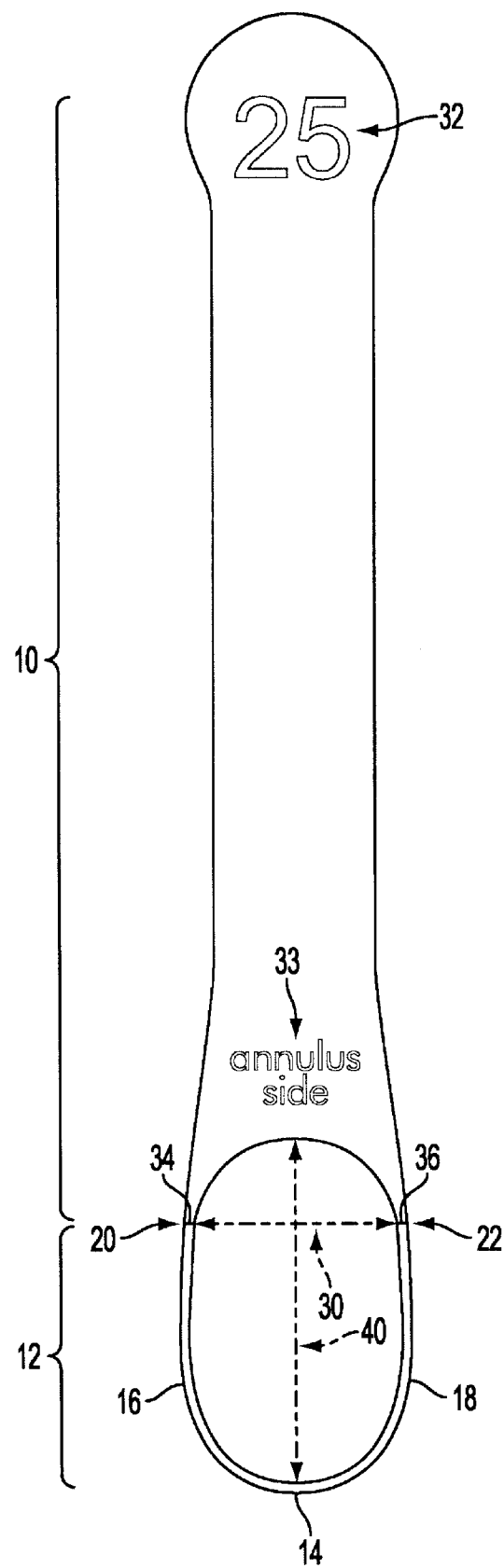
FIG. 4 is a top view of the sizer of FIG. 3.
Figure 5:
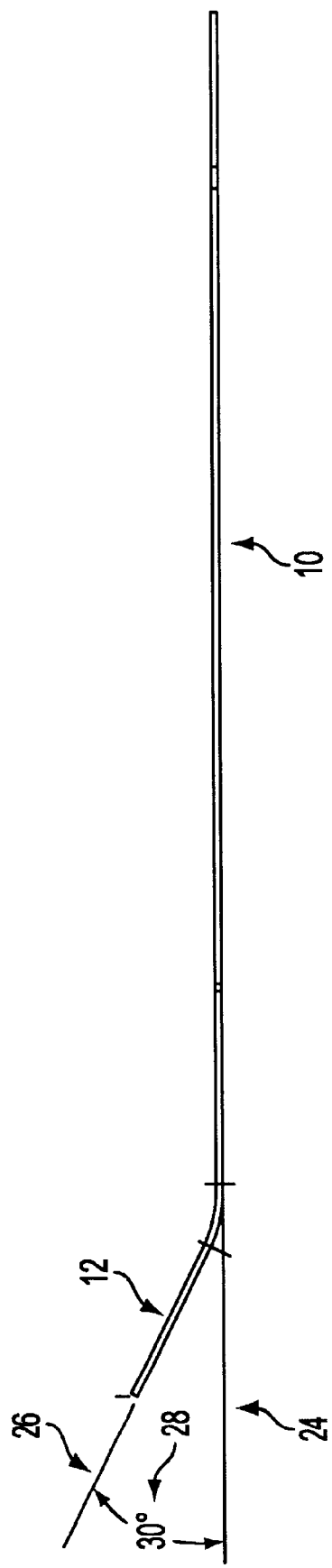
FIG. 5 is a side view of the sizer of FIG. 3.

FIGS. 3, 4 and 5 illustrate another embodiment of a sizer for assessing the geometry of a heart valve annulus by measuring annulus size, leaflet height, and leaflet symmetry. The sizer includes a handle portion 10 for holding the instrument and an adjoining sizing portion 12 that is inserted into the valve annulus. Preferably, the handle portion 10 is integrally formed with the sizing portion 12. Alternatively, handle portion 10 and sizing portion 12 can be separate pieces connected to each other, using a variety of known techniques.

The sizing portion 12 preferably conforms to the shape of the contoured line of valve attachment. The sizing portion preferably is in a shape such as an arch or other having an opening therein to provide unobstructed viewing during the sizing procedure. However, any of various other shapes can be used. For example, the sizing portion need not necessarily have an opening therein and can be, for example, a planar or contoured substantially semielliptical shape. In the illustrated embodiment, the sizing portion 12 is in the shape of arch having an apex 14 and two legs 16 and 18. Each leg has a base 20 and 22 adjoining the handle portion 10 of the instrument. In a presently preferred embodiment, each leg 16 and 18 is approximately 1–2 millimeters wide at the base. Each leg 16 and 18 is bent at or near its base 20 and 22 such that the sizing portion is angled to conform to the conical shape of the aortic root at the level of the valve. As shown in FIG. 5, the handle portion 10 and the sizing portion 12 are preferably adjoined such that the plane 24 of the handle portion 10 and the plane 26 of the sizing portion 12 form an angle 28 of approximately 30 degrees.

The sizing portion 12 comprises a predetermined distance indicator. As used herein the term "predetermined distance indicator" means a structural feature, marking or other indicia that visually indicates a designated distance or distances. For example, the predetermined distance indicator can be a horizontal spacing between two structural components of the sizing portion, the width of the sizing portion or a segment thereof, or a horizontal distance between two marks on the sizing portion. As shown in FIG. 4, legs 16 and 18 are separated from each other by a predetermined distance 30 measured from the inside edge of one leg at the base to the inside edge of the other leg at the base. In the illustrated embodiment, predetermined distance 30 is a predetermined distance indicator. Distance 30 is preferably the expected distance separating two commissures of a normal heart valve having a diameter substantially equivalent to the measured diameter of the valve annulus being assessed. The intercommissural distance of a normal, symmetrical, heart valve has been shown to be a chord length of the aortic diameter at the sino-tubular level, and is approximately 0.87 of the aortic diameter at the sino-tubular level.

The sizer is preferably provided in graduated sizes to correspond to various common valve annulus diameters, preferably in kits including various common sizes. The handle portion 10 has a size marking 32 that indicates the annulus diameter associated with the sizer (25 mm in the example shown in FIGS. 3 and 4). Side marking 33 indicates the side of the instrument that is to be placed against the valve annulus.

The heart valve annulus is measured using a standard plug gauge or other means. A sizer corresponding in size to the measured diameter of the annulus is then selected using the size marking 33 as a guide. The sizing portion 12 is inserted into the heart valve annulus and bases 20 and 22 of each of the two legs 16 and 18 are aligned with two of the commissures of the heart valve annulus to compare the distance between the two commissures to the predetermined distance 30 between the two legs 16 and 18. Each base 20 and 22 preferably includes a line 34 and 36 to provide a visual indication of the spots on the sizer that are to placed adjacent to the two commissures. For a tri-leaflet valve, symmetry is assessed by comparing the three intercommissural distances. In a symmetric root these distances should be in close agreement.

The sizing portion 12 comprises a predetermined height indicator. As used herein the term "predetermined height indicator" means a structural feature, marking or other indicia that visually indicates a designated height or heights. For example, the predetermined height indicator can be a vertical spacing between two structural components of the sizing portion, the height of the sizing portion or a segment thereof, or a vertical distance between two marks on the sizing portion. As shown in FIG. 4, the arch-shaped sizing portion 12 has a height 40 measured from each base 20 and 22 to the apex 14 of the arch. In the illustrated example, height 40 is the predetermined height indicator of the sizing portion. Height 40 preferably approximates the expected leaflet height of a normal heart valve having a diameter corresponding to the valve diameter size of the sizer as indicated by size marking 32. Expected leaflet height for a normal heart valve can be determined for any given annulus diameter, as reported, for example, by W. mi) M. Swanson and R. E. Clark, "Dimensions and Geometric Relationships of the Human Aortic Value as a Function of Pressure," *Circulation Research,* Vol. 35, December 1974.

The sizer can also be used to mark the line of valve leaflet attachment on the exposed annulus following removal of the native valve tissue to identify the suture line for reconstruction. A marking material, such as methylene blue dye (or other biocompatible dye or marking material) is applied to sizing portion 12 to allow it to function as a marking portion of the instrument. Sizing portion 12 is placed along the attachment line of the aortic annulus and is used to mark the suture line for valve reconstruction. Sizing portion 12 preferably has a textured region (e.g., on the sides of thereof) to retain dye or other marking material. The textured region can be created by roughening, bead blasting, etching or similar technique. A surgeon who chooses to mark the leaflet attachment line can do so with the instrument by wetting the textured loop surface on the identified annulus side with 2% methylene blue dye. Methylene blue makes a clear, fast-drying mark that remains visible for usually 15–20 minutes, time enough for the reconstruction to be performed.

The sizer can be made of stainless steel for reuse after sterilization. Alternatively, it can be made of any of a variety of other biocompatible materials, such as a thermoplastic material, and can be provided as a sterile, single-use, disposable instrument.

The sizers described herein can be used in any semilunar heart valve operation where it is desirable to know the root diameter, leaflet height and line of attachment, and commissural symmetry. Such operations include, but are not limited to, valve reconstruction with tissue, autologous, homologous or heterologous, valve replacement with a homograft or any type of stentless heterograft, and pulmonary valve autotransplantation to the aortic position.

Although the invention has been described with reference to specific embodiments, it will be understood by those skilled in the art that various changes may be made without departing from the spirit or scope of the invention. For instance, details relating to the arch shape of the presently preferred embodiment of the instrument, are provided to facilitate the understanding of the invention and are not provided to limit the scope of the invention. Therefore, it should be clearly understood that the forms of the present invention described above and shown in the figures of the accompanying drawings are illustrative only and may not be used to unduly limit the scope of the present invention.

We claim:

1. A sizer for assessing the geometry of a heart valve annulus having a plurality of commissures, the sizer comprising:

a handle portion for holding the sizer; and a sizing portion adjoining the handle portion, the sizing portion comprising a predetermined distance indicator for assessing the distance between two of the plurality of commissures by placing the sizing portion adjacent to the two of the plurality of commissures and comparing the predetermined distance indicator on the sizing portion to the distance between the two of the plurality of commissures.

2. The sizer of claim 1, wherein the sizing portion comprises an arch having two legs separated by a predetermined distance, each leg having a base adjoining the handle portion, and wherein the predetermined distance indicator is the predetermined distance between the two legs, whereby the sizing portion can be inserted into the annulus and the two legs placed adjacent to two of the plurality of commissures to compare the distance between the two of the plurality of commissures to the distance between the two legs.

3. The sizer of claim 2, wherein the annulus has a known valve diameter, and wherein the predetermined distance between the two legs approximates an expected distance between two commissures of a normal heart valve having a valve diameter substantially equivalent to the diameter of the annulus.

4. The sizer of claim 2, wherein the annulus has a contoured line of valve leaflet attachment, and wherein the shape of the arch substantially conforms to the contoured line of valve leaflet attachment.

5. The sizer of claim 4, wherein the annulus has a conical shape, and wherein the sizer further comprises a bend at the base of the legs of the arch such that the sizing portion is angled to substantially conform to the conical shape of the annulus.

6. The sizer of claim 2, wherein each leg of the arch further comprises a line at the base marking a point on each of the legs to be placed adjacent to a commissure.

7. The sizer of claim 2, wherein the arch has an apex, and wherein the height of the arch from the base of each leg to the apex corresponds to a predetermined leaflet height.

8. The sizer of claim 7, wherein the annulus has a known diameter, and wherein the predetermined leaflet height approximates an expected height of a leaflet of a normal heart valve having a valve diameter substantially equivalent to the diameter of the annulus.

9. The sizer of claim 2, wherein the arch has a textured surface for retaining a marking material to mark the line of valve leaflet attachment.

10. The sizer of claim 1, further comprising a size marking that indicates a valve diameter corresponding to the size of the sizer.

11. A sizer for assessing the geometry of a heart valve annulus having a contoured line of valve leaflet attachment and a leaflet height, the sizer comprising:
   a handle portion for holding the sizer; and
   a sizing portion adjoining the handle portion, the sizing portion comprising a predetermined height indicator for assessing the leaflet height by placing the sizing portion along the contoured line of valve leaflet attachment and comparing the predetermined height indicator to the leaflet height of the annulus.

12. The sizer of claim 11, wherein the sizing portion conforms in shape to the contoured line of valve attachment.

13. The sizer of claim 11, wherein the sizing portion comprises an arch having an apex and two legs, each of which has a base adjoining the handle portion, wherein the arch has a predetermined height measured from the base of each leg to the apex, and wherein the predetermined height indicator is the predetermined height of the arch, whereby the sizing portion can be inserted into the annulus and placed along the contoured line of valve attachment to compare the leaflet height of the annulus to the height of the arch.

14. The sizer of claim 13, wherein the annulus has a known diameter, and wherein the height of the arch corresponds to a predetermined leaflet height that approximates an expected height of a leaflet of a normal heart valve having a valve diameter substantially equivalent to the diameter of the annulus.

15. A sizer for assessing the geometry of a heart valve annulus having a contoured line of valve leaflet attachment, a valve diameter, and a leaflet height, the sizer comprising:
   a handle portion for holding the sizer; and
   a sizing portion conforming in shape to the contoured line of valve leaflet attachment comprising an arch having an apex and two legs, each of which has a base adjoining the handle portion, the arch having a height measured from the base of each leg to the apex, and wherein the height of the arch corresponds to a predetermined leaflet height that approximates an expected height of a leaflet of a normal heart valve having a valve diameter substantially equivalent to the diameter of the annulus, whereby the sizing portion can be inserted into the annulus and placed along the contoured line of valve leaflet attachment to compare the leaflet height of the annulus to the height of the arch.

16. A sizer for assessing the geometry of a heart valve annulus having a conical shape, a contoured line of valve leaflet attachment, a leaflet height, a valve diameter and a plurality of commissures, the sizer comprising:
   a handle portion for holding the sizer; and
   a sizing portion conforming in shape to the contoured line of valve attachment comprising an arch having an apex and two legs, each of which has a base adjoining the handle portion, wherein the base of each leg is bent such that the sizing portion is angled to conform to the conical shape of the annulus, and wherein the legs are separated from each other by a predetermined distance such that the sizing portion can be inserted into the annulus and the two legs placed adjacent to two of the plurality of commissures to compare the distance between the two of the plurality of commissures to the predetermined distance between the two legs, and wherein the arch has a height measured from the base of each leg to the apex, and wherein the height of the arch corresponds to a predetermined leaflet height that approximates an expected height of a leaflet of a normal heart valve having a valve diameter substantially equivalent to the diameter of the annulus, whereby the sizing portion can be inserted into the annulus and placed along the contoured line of valve leaflet attachment to compare the leaflet height of the annulus to the height of the arch.

17. A method of assessing the geometry of a heart valve annulus having a valve diameter and a plurality of commissures, the method comprising:
   measuring the valve diameter of the annulus;
   providing a sizer corresponding in size to the valve diameter of the annulus, the sizer comprising a sizing portion comprising a distance indicator that approximates an expected distance between two commissures of a normal heart valve having a valve diameter substantially equivalent to the measured valve diameter of the annulus;
   placing the sizing portion adjacent to two of the plurality of commissures; and
   comparing the distance between the two of the plurality of commissures to the distance indicator.

18. A method of assessing the geometry of a heart valve annulus having a contoured line of valve leaflet attachment, a valve diameter, and a leaflet height, the method comprising:
   measuring the valve diameter of the annulus;
   providing a sizer comprising a sizing portion, at least a portion of which has a predetermined height that approximates an expected height of a leaflet of a normal heart valve having a valve diameter substantially equivalent to the measured valve diameter of the annulus;
   inserting the sizing portion into the annulus along the contoured line of valve leaflet attachment; and
   comparing the leaflet height of the annulus to the predetermined height of the sizing portion.

19. A kit for assessing the geometry of a heart valve annulus having a valve diameter and a plurality of commissures, the kit comprising:
   a plurality of sizers corresponding in size to various valve diameters, wherein each sizer comprises:
   a handle portion for holding the sizer; and
   a sizing portion adjoining the handle portion, the sizing portion comprising a predetermined distance indicator for assessing the distance between two of the plurality of commissures by placing the sizing portion adjacent to the two of the plurality of commissures and comparing the distance indicator to the distance between the two of the plurality of commissures.

20. A kit for assessing the geometry of a heart valve annulus having a contoured line of valve leaflet attachment, a leaflet height, and a valve diameter, the kit comprising:
   a plurality of sizers corresponding in size to various valve diameters, wherein each sizer comprises:

a handle portion for holding the sizer; and a sizing portion adjoining the handle portion, the sizing portion comprising a predetermined height indicator for assessing the leaflet height by placing the sizing portion along the contoured line of valve leaflet attachment and comparing the height indicator to the leaflet height of the annulus.

21. An instrument for marking a contoured line of valve leaflet attachment of a heart valve annulus, the instrument comprising:

a handle portion for holding the instrument; and a marking portion conforming in shape to the contoured line of valve leaflet attachment, whereby a marking material can be applied to the marking portion and the marking portion can be inserted into the annulus and placed along the line of valve leaflet attachment to mark the line of leaflet attachment with the marking material.

22. The instrument of claim 21, further comprising a textured region on the sizing portion for retaining a marking material.

23. A method for marking a contoured line of valve leaflet attachment of a heart valve annulus, the method comprising:

providing an instrument having a marking portion conforming in shape to the contoured line of valve leaflet attachment;

applying a marking material to marking portion of the instrument; and placing the marking portion of the instrument along the contoured line of valve leaflet attachment to mark the line of leaflet attachment with the marking material.

24. The method of claim 23, wherein the marking material comprises methylene blue dye.

* * * * *